US00PP08557P

United States Patent [19]

Vart

[11] Patent Number: Plant 8,557

[45] Date of Patent: Jan. 25, 1994

[54] "SWEET QUEEN" PLUM TREE

[76] Inventor: David C. Vart, 2503 18th Ave., Kingsburg, Calif. 93631

[21] Appl. No.: 28,926

[22] Filed: Mar. 5, 1993

[51] Int. Cl.[5] ..... A01H 5/00

[52] U.S. Cl. ..... Plt./38.1

[58] Field of Search ..... Plt. 38.1

[56] References Cited

PUBLICATIONS

Brooks, R. M., et al., "Queen Ann", Register of New Fruit and Nut Varieties, University of California Press, Berkeley, Calif., 1972, p. 514.

*Primary Examiner*—James R. Feyrer

*Attorney, Agent, or Firm*—Worrel & Worrel

[57] ABSTRACT

A new and distinct variety of plum tree which is a sport of the "Queen Ann" plum tree, but from which it is distinguished by producing large fruit of bright green coloration which are mature for harvesting and shipment approximately July 1 to July 5 in Kingsburg in the San Joaquin Valley of central California and which are slightly elongated with a superior ability to resist bruising.

1 Drawing Sheet

BACKGROUND OF THE NEW VARIETY

The present invention relates to a new and distinct variety of plum tree, which will hereinafter be denominated varietally as the "Sweet Queen" plum tree, and more particularly to a plum tree which produces fruit which are mature for commercial harvesting and shipment approximately July 1 to July 5 in the San Joaquin Valley of central California, and which further is distinguished by producing large fruit which are slightly elongated, have a bright green skin coloration and flesh of which is quite firm so as to possess excellent handling and shipping characteristics.

The discovery of new varieties of fruit bearing trees is not, in itself, particularly unusual. However, the discovery of new varieties possessing one or more characteristics of superior commercial significance is indeed rare. While there is a multiplicity of criteria against which any newly discovered variety must be evaluated, handling, shipping and keeping quality are among the most important for commercial varieties of tree fruit. In order to be commercially acceptable, tree fruit must withstand the rigors of picking, handling, storing, shipping and subsequent handling incident to reaching the ultimate consumer. This journey may take several weeks and fruit which becomes bruised or otherwise damaged or which noticeably deteriorates during this passage is of little or no commercial value.

Therefore, the discovery of a new variety of tree fruit which otherwise possesses commercially acceptable attributes and which, in addition, has superior handling, shipping and keeping quality in a notable event. The "Sweet Queen" plum tree of the present invention is such a new variety.

ORIGIN AND ASEXUAL REPRODUCTION OF THE NEW VARIETY

The present variety of plum tree was discovered by the inventor in 1983 on his ranch located near Kingsburg in the San Joaquin Valley of central California. The new variety was discovered as a sport of a twenty year old "Queen Ann" plum tree. The new variety was asexually reproduced in 1989 on the same property by grafting some seedlings with scions thereof. The grafted seedlings were observed and first bore fruit in 1991. The asexually reproduced trees have been confirmed to possess precisely the same characteristics as the original sport of the new variety.

SUMMARY OF THE NEW VARIETY

The "Sweet Queen" plum tree is characterized as to novelty by producing large fruit which are slightly elongated, have a bright green skin coloration, and excellent handling and shipping quality. Further the fruit produced by the "Sweet Queen" plum tree is ripe for commercial harvesting and shipment approximately July 1 to July 5 near Kingsburg in the San Joaquin Valley of central California. The flesh of the fruit is quite firm and is greenish yellow with a very mild flavor. The new variety is particularly noteworthy in the fact that the fruit is highly resistant to bruising and thus handles and ships quite well and has a good shelf life. The new variety is a sport of the "Queen Ann" plum tree.

BRIEF DESCRIPTION OF THE DRAWING

The accompanying drawing is a color photograph showing the plum tree of the new variety including fruit of the new variety, one sectioned to show one half with the stone left in place and the other half with the stone removed to expose the pit cavity; a second in side elevation; a third in top plan view showing the base thereof; a fourth in side elevation showing the suture thereof; and a fifth in bottom plan view showing the apex end thereof; a stone of the fruit; and representative foliage of the new variety.

DETAILED DESCRIPTION

Referring more specifically to the pomological details of this new and distinct variety of plum tree, the following has been observed under the ecological conditions prevailing at the orchard of origin which is located near Kingsburg in the San Joaquin Valley of central California. All major color code designations are by reference to the *Inter-Society Color Council, National Bureau of Standards.* Common color names are also occasionally employed.

TREE

Generally:
- *Size.*—Normal, depending on pruning and shaping.
- *Vigor.*—Very vigorous.
- *Productivity.*—Good.
- *Regularity of bearing.*—Consistently bears well.

Trunk:
- *Surface texture.*—Normal bark for plum tree, slightly rough.
- *Color.*—Red brown (47 d.gy.r.br).
- *Lenticels — Numbers.*—12 to 14 per square inch.
- *Lenticels — size.*—Length — ⅛ inch.
- *Lenticels — color.*—72 d.oy.

Branches:
- *Size.*—Normal, depending on shaping.
- *Surface texture.*—Normal bark for plum tree, slightly rough.
- *Color.*—Red brown (47 d.gy.r.br).
- *Lenticels — numbers.*—12 to 14 per square inch.
- *Lenticels — size.*—Length — ⅛ inch.

LEAVES

Average length.—3⅜ inches to 3½ inches.
Average width: 1⅜ inches to 1½ inches.
Shape: Lanceolate.
Color:
- *Upwardly disposed surface.*—Dark green (128 d.gy.01.g).
- *Downwardly disposed surface.*—Gray green (110 gy.01).

Marginal form:
- *Generally.*—Finely serrate.

Leaf base: Cuneate.
Petiole:
- *Length.*—⅝ inch.
- *Thickness.*—1/16 inch.

Stem glands:
- *Number.*—One pair.
- *Position.*—Base of leaf.
- *Type.*—Reniform.
- *Size.*—Small.

FLOWERS

Flower buds:
- *Generally.*—Information compiled at the time white coloration beginning to appear at apexes of buds. Buds set on fruit spurs on branches, each spur can have as many as twenty buds per spur.
- *Size — length.*—3/16 inch.
- *Size — diameter.*—3/16 inch.
- *Shape.*—Round in appearance.
- *Color.*—Dull green (120 M.Y.G.).

Flowers:
- *Generally.*—Up to twenty buds on each fruit spur, each bud forming a single flower. Fruit spurs very heavy on each branch, about ¾ inch apart.
- *Date of bloom.*—About the 25th of February to 1st of March in Kingsburg in the San Joaquin Valley of central California.
- *Size — Petal — Length.*—5/16 inch.
- *Size — Petal — Diameter.*—¼ inch.

Flowers — petal:
- *Shape.*—Very slightly elongated.
- *Petals — color.*—White (263 white).

Petiole:
- *Length.*—5/16 inch at full bloom.

FRUIT

Maturity when described: Ripe for commercial harvesting and shipment approximately July 1 to July 5 near Kingsburg in the San Joaquin Valley of central California.

Size:
- *Generally.*—Large.
- *Average diameter in the axial plane.*—2¼ inches to 2⅜ inches.
- *Average diameter transverse in the suture plane.*—2⅜ inches to 2½ inches.
- *Average diameter transverse and at right angles to the suture plane.*—2¼ inches to 2⅜ inches.
- *Form.*—Uniformity — Good. Symmetry — Not fully round. Most are slightly elongated with apex point. A few will are round.
- *Suture.*—Generally — Very smooth and very slightly recessed. Length — 2¾ inches to 3 inches from stem cavity to apex point.
- *Stem cavity.*—Width — ½ inch. Depth — ⅜ inch.
- *Stem.*—Length — 1 1/16 inches. Width — 3/32 inches.
- *Apex.*—Shape — Slightly rounded.
- *Base.*—Wide and rounded.

Skin:
- *Thickness.*—Normal for plum.
- *Texture.*—Very smooth.
- *Tendency to crack.*—None.
- *Color.*—Bright green (116 brill y.g).

Flesh:
- *Flesh color.*—Light yellow green (121 p.y.g).
- *Surface of pit cavity.*—Almost smooth.
- *Color of pit well.*—Darker dull green (120 m.y.g).
- *Juice production.*—Quite juicy.
- *Flavor.*—Good, mild, low acid.
- *Aroma.*—Slight.
- *Fibers.*—Numbers — None.
- *Ripening.*—Even.
- *Eating quality.*—Good.

Stone:
- *Attachment.*—Freestone.
- *Fibers.*—Numbers — None.
- *Size.*—Length — ⅞ inch. Width — ¾ inch. Thickness — ⅜ inch.
- *Form.*—Generally — Elongated and almost flat in appearance.
- *Color.*—Dry — Pale brown (76 l.y.br)
- *Base.*—Shape — Small, round. Size — Diameter — ⅛ inch.
- *Ridges.*—None, but slightly rough.

Use: Fresh market.
Keeping quality: Has good shelf life, without cooling. Has been kept in storage about four weeks without breakdown.
Shipping and handling qualities: This fruit does not show bruise marks, so should ship very well.

Although the new variety of plum tree possesses the described characteristics noted above as a result of the growing conditions prevailing near Kingsburg in the central part of the San Joaquin Valley of California, it is to be understood that variations of the usual magnitude and characteristics incident to changes in growing conditions, irrigation, fertilization, pruning and pest control are to be expected.

Having thus described and illustrated my new variety of plum tree, what I claim as new and desire to be secured by Plant Letters Patent is:

1. A new and distinct variety of plum tree substantially as illustrated and described which is somewhat remotely similar to the "Queen Ann" plum tree from which it originated as a sport, but from which it is distinguished and characterized principally as to novelty by producing large fruit of generally bright green coloration which are mature for commercial harvesting and shipment approximately July 1 to July 5 in the San Joaquin Valley of central California and which further has noteworthy shipping and handling characteristics.

* * * * *

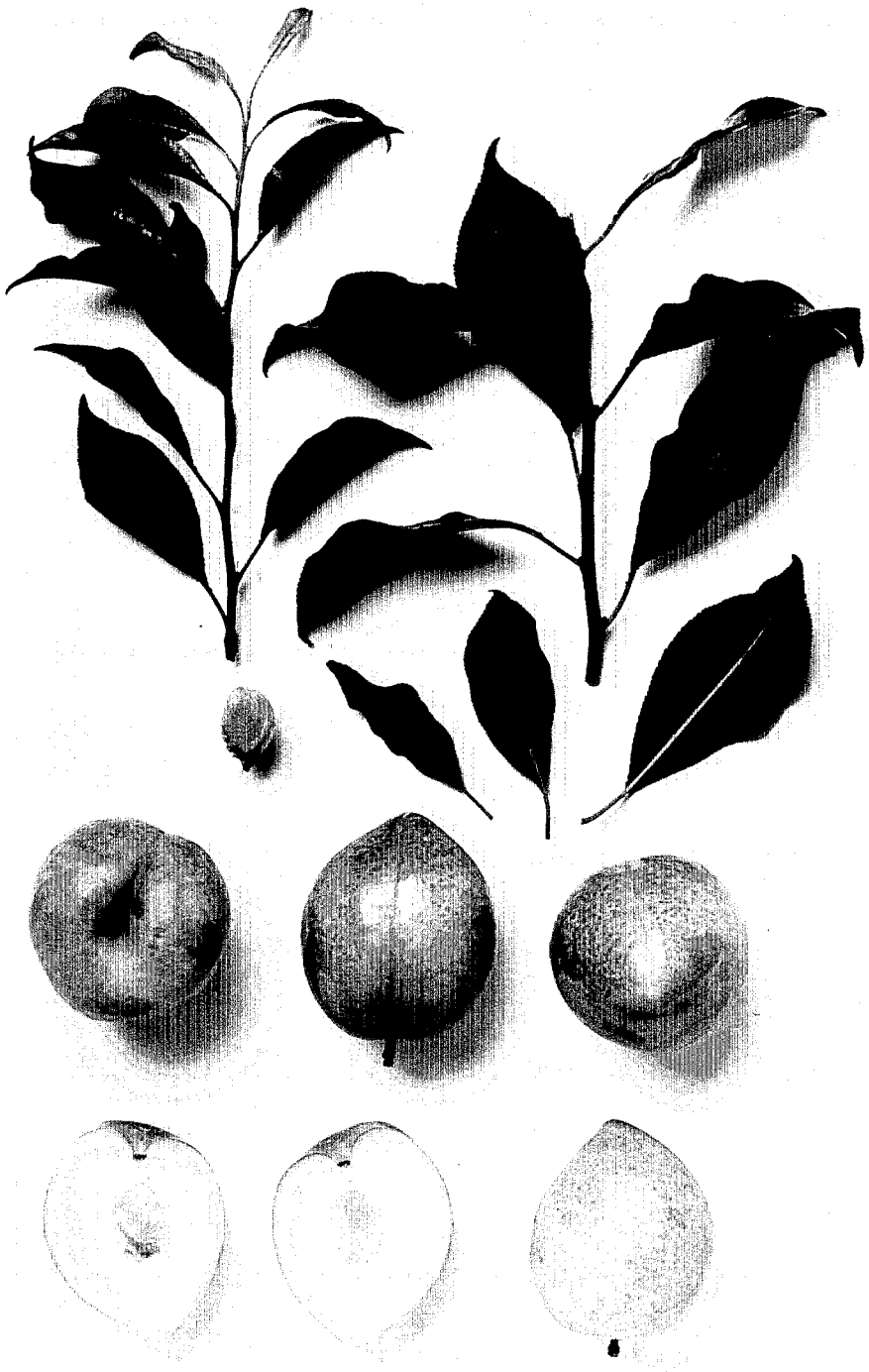

UNITED STATES PATENT AND TRADEMARK OFFICE

CERTIFICATE OF CORRECTION

PATENT NO. : Plant 8,557

DATED : January 25, 1994

INVENTOR(S) : David C. Vart

It is certified that error appears in the above-identified patent and that said Letters Patent is hereby corrected as shown below:

Column 1, Line 32, delete "in" and substitute

---is---.

Signed and Sealed this

Twenty-first Day of June, 1994

*Attest:*

Bruce Lehman

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : Plant 8,557

DATED : January 25, 1994

INVENTOR(S) : David C. Vart

It is certified that error appears in the above-identified patent and that said Letters Patent is hereby corrected as shown below:

Column 1, Line 39, delete "his ranch" and substitute ---his father's ranch---.

Column 4, line 17, delete "are" and substitute ---be---.

Signed and Sealed this

Twenty-third Day of May, 1995

Bruce Lehman

*Attest:*

BRUCE LEHMAN

*Attesting Officer*

*Commissioner of Patents and Trademarks*